US007996061B2

(12) United States Patent
Mollard et al.

(10) Patent No.: US 7,996,061 B2
(45) Date of Patent: Aug. 9, 2011

(54) METHOD AND SURGICAL NAVIGATION SYSTEM FOR CREATING A RECESS TO RECEIVE AN ACETABULUM

(75) Inventors: Benoit Mollard, Echirolles (FR); François Leitner, Uriage (FR); Sergej Kammerzell, Engen (DE); Dirk Friedrich, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 854 days.

(21) Appl. No.: 12/001,997

(22) Filed: Dec. 12, 2007

(65) Prior Publication Data

US 2008/0214932 A1 Sep. 4, 2008

Related U.S. Application Data

(63) Continuation of application No. PCT/EP2006/005181, filed on May 31, 2006.

(30) Foreign Application Priority Data

Jun. 15, 2005 (DE) .................. 10 2005 028 831

(51) Int. Cl.
*A61B 5/05* (2006.01)
*A61B 19/00* (2006.01)
(52) U.S. Cl. .................. 600/424; 600/429; 606/130
(58) Field of Classification Search .......... 600/424–429; 606/130
See application file for complete search history.

(56) References Cited

U.S. PATENT DOCUMENTS

| 5,966,827 | A | 10/1999 | Horvath et al. |
| 6,621,247 | B1 | 9/2003 | Bulling et al. |
| 6,669,653 | B2 | 12/2003 | Paltieli |
| 2002/0077540 | A1 | 6/2002 | Kienzle, III |
| 2004/0254584 | A1 | 12/2004 | Sarin et al. |
| 2004/0254586 | A1 | 12/2004 | Sarin et al. |
| 2005/0203540 | A1 | 9/2005 | Broyles |
| 2008/0269757 | A1 | 10/2008 | McMinn |
| 2009/0171370 | A1 | 7/2009 | Yoon et al. |
| 2009/0306679 | A1 | 12/2009 | Murphy |
| 2010/0030231 | A1 | 2/2010 | Revie et al. |

FOREIGN PATENT DOCUMENTS

| DE | 20 2005 009 777 | 12/2005 |
| WO | 2004/030556 | 4/2004 |

*Primary Examiner* — Michael T Rozanski
(74) *Attorney, Agent, or Firm* — Lipsitz & McAllister, LLC

(57) ABSTRACT

A system and method for creating a cavity to receive an acetabulum in a pelvic bone with the aid of a navigated tool are provided. A tear-drop point on a pelvic bone is located by means of a scanning instrument. A tear-drop plane is determined from position data of the tear-drop point and the plane of the pelvic inlet. The tear-drop plane lies perpendicular to the plane of the pelvic inlet, extends parallel to a line connecting the two anterior superior iliac spines, and runs through the tear-drop point. A reference point is determined which is at a defined height above the tear-drop plane, in a defined position in an anterior-posterior direction, and at a defined spacing from an outer surface of the pelvic bone in a lateral-medial direction. A tool is worked into the pelvic bone in a desired direction relative to the reference point.

38 Claims, 8 Drawing Sheets

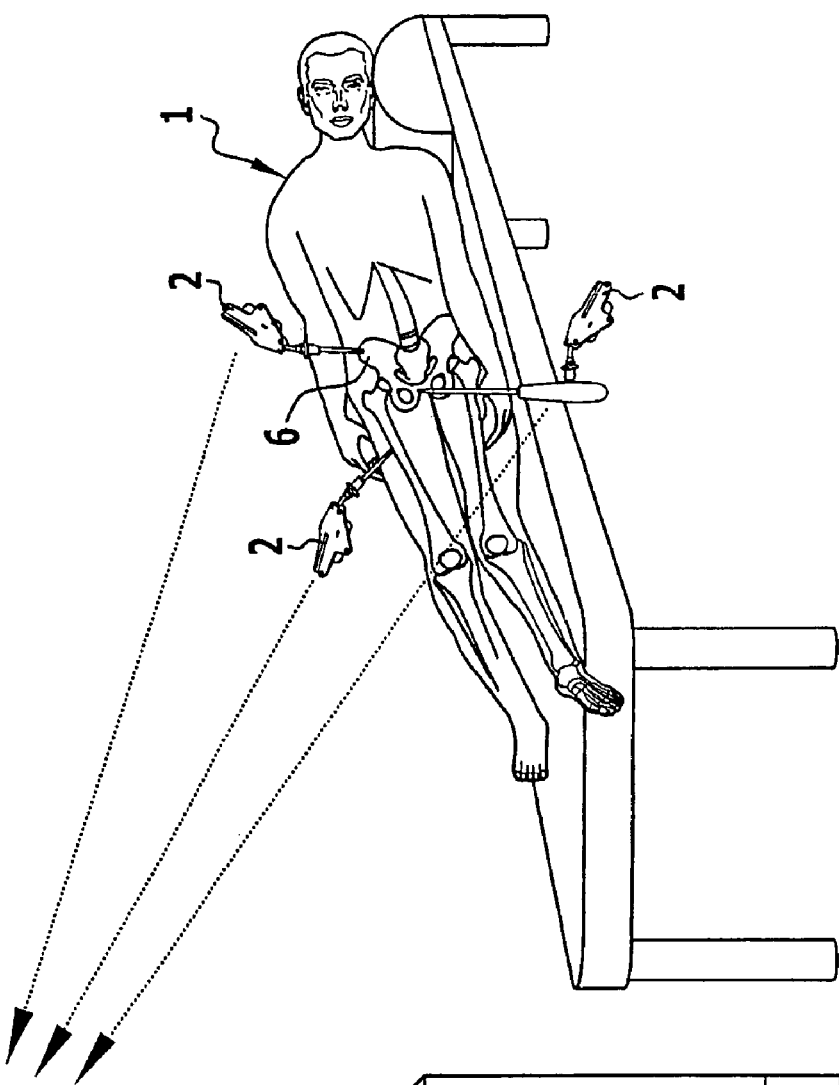
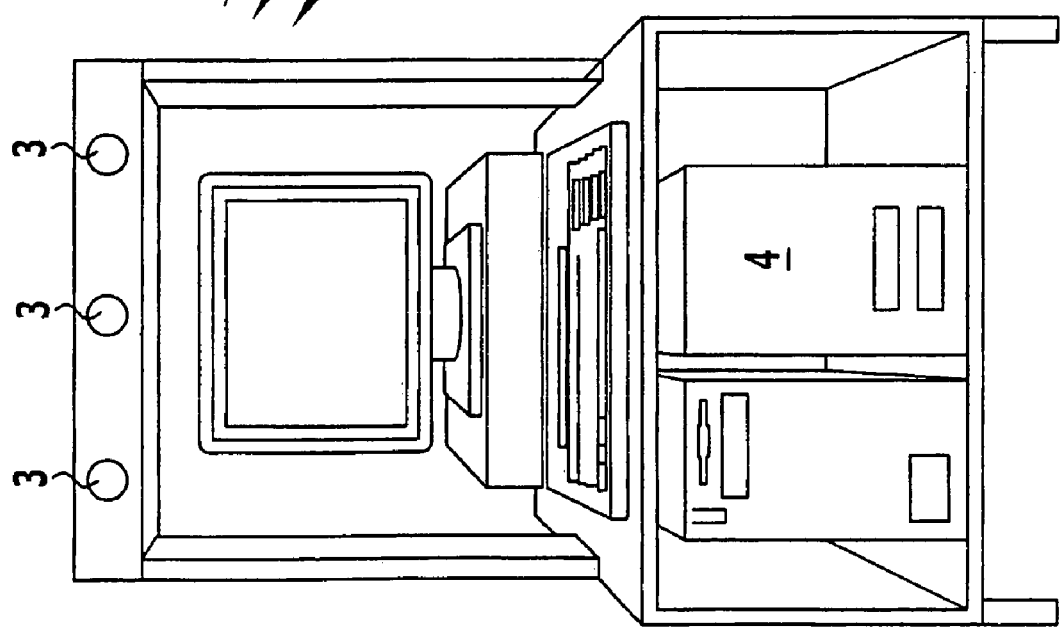
FIG.1

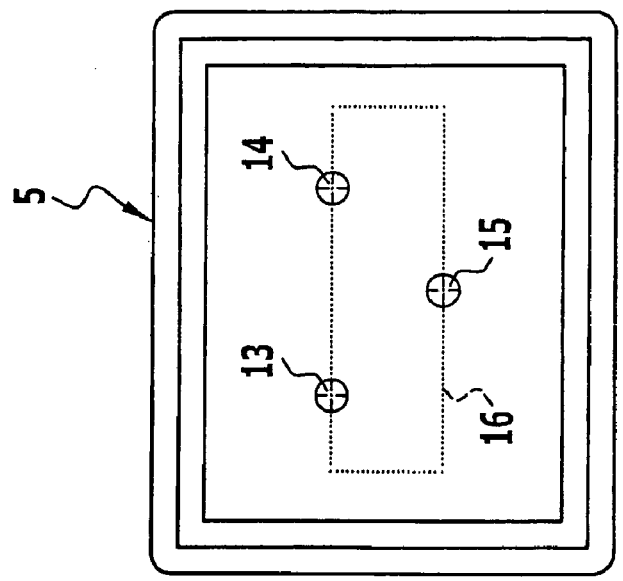
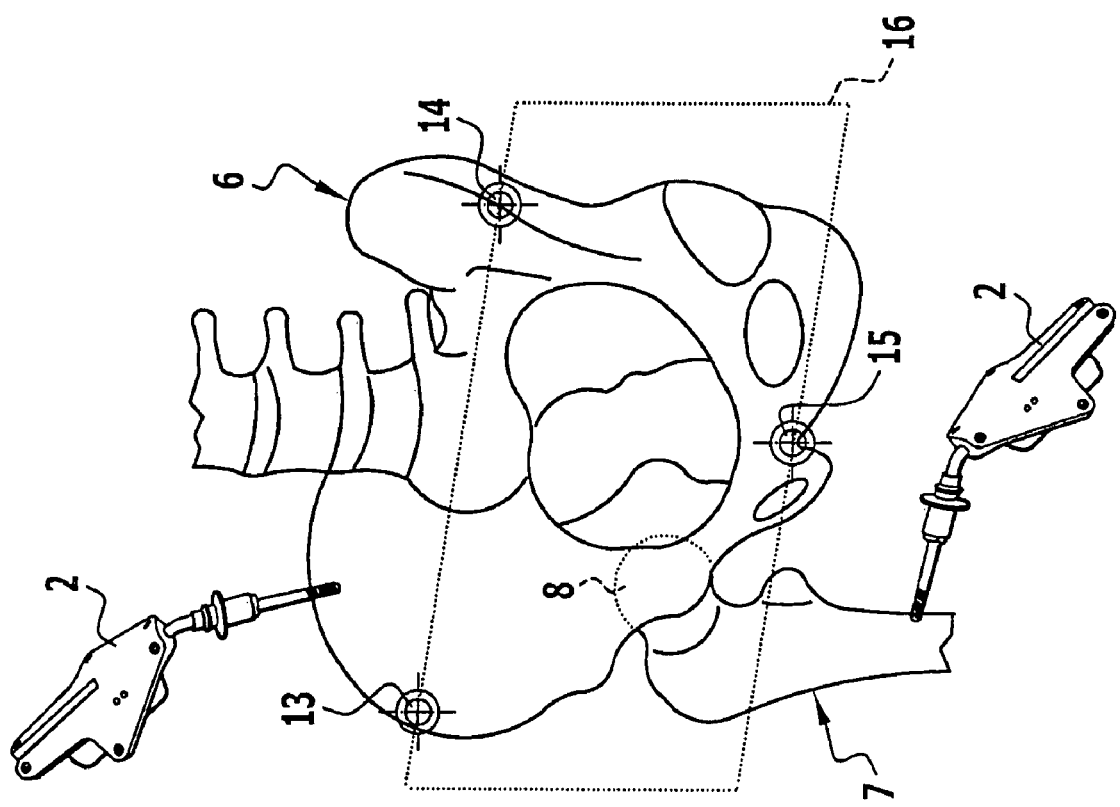
FIG. 2

METHOD AND SURGICAL NAVIGATION SYSTEM FOR CREATING A RECESS TO RECEIVE AN ACETABULUM

This application is a continuation of International patent application no. PCT/EP2006/005181 filed on May 31, 2006 and claims the benefit of German patent application no. 10 2005 028 831.6 filed Jun. 15, 2005, each of which is incorporated herein and made a part hereof by reference.

BACKGROUND OF THE INVENTION

The invention relates to a method for producing a cavity to receive an acetabulum in a navigated pelvic bone with the aid of a navigated tool.

During implantation of an artificial hip joint, an artificial acetabulum is inserted into the pelvic bone, and for this a cavity that receives the acetabulum must be machined in an anatomically defined orientation into the pelvic bone at the anatomically defined location. These cavities are normally hemispherical and are generated by means of a hemispherical milling cutter. To be able to determine and maintain the precise disposition—i.e. the orientation and position—of the receiving cavity, it is known to navigate the pelvic bone as well as the tool generating the cavity by means of a surgical navigation system. Such a navigation system enables the relative spatial coordination of the tool and the pelvic bone to be determined and monitored.

When replacing a defective acetabulum with an artificial acetabulum, the acetabulum is normally implanted at substantially the same location as that where the natural acetabulum was previously arranged, this position being referred to hereafter as the primary acetabulum.

However, there are also cases in which the natural acetabulum is not situated in the anatomically desirable position, whether as a result of a congenital defect or as a result of the natural joint socket being displaced out of the position of the primary acetabulum, usually upwards, i.e. in the cranial direction. In these cases it is extraordinarily difficult when implanting an artificial joint socket that is to be inserted at the anatomically normal position, i.e. in the position of the primary acetabulum, to determine this position on the pelvic bone, so that the tool can then be guided in the desired manner.

SUMMARY OF THE INVENTION

It is an object of the invention to develop a method of the generic type such that the surgeon is given an auxiliary disposition for the correct position and orientation of the tool relative to the pelvic bone, so that the receiving cavity for the acetabulum can be machined into the pelvic bone at the desired anatomical location and in the desired orientation, even if the natural acetabulum was not previously situated in this desired anatomical disposition.

This object is achieved according to the invention with a method of the above-described type in that the tear-drop point on the pelvic bone is located by means of a navigated scanning instrument, from the position data and the plane of the pelvic inlet of said pelvic bone a tear-drop plane is determined, which lies perpendicular to said plane of the pelvic inlet and extends parallel to a line connecting the two anterior superior iliac spines and through the scanned tear-drop point, that a reference point is determined at a defined height above the tear-drop plane and in a defined position in the anterior-posterior direction and at a defined spacing from the outer surface of the pelvic bone in the lateral-medial direction, and that the tool is worked into the pelvic bone in a desired direction relative to the reference point until a predetermined disposition of the tool relative to the reference point is reached.

In this way, on the basis of relatively few prominent points of the pelvic bone and on the basis of certain anatomical assumptions, it is possible to select the disposition of the tool, with which the receiving cavity is created, in such a way that the receiving cavity can be formed in the desired position and orientation on the pelvic bone.

Working from the plane of the pelvic inlet of the pelvic bone, which is spanned by the two anterior superior iliac spines on one side and the pubic symphysis on the other side, and also by determination of the position of the tear-drop points, it is possible to determine the tear-drop plane, i.e. a horizontal plane of the pelvis that extends through the tear-drop point and forms a reference plane, working from which the position and orientation of the receiving cavity can be determined.

For this, a reference point is determined, which is located at a specific height above this tear-drop plane and the position of which in the anterior-posterior direction is selected on the basis of anatomical assumptions.

Finally, the spacing of this reference point from the outer surface of the pelvic bone is also determined, i.e. in the lateral-median direction. Anatomical assumptions are also evaluated here in order to determine this reference point. This can lie, for example, inside the pelvic bone or in another particularly preferred case can coincide with the rear side of the pelvic bone in the region of the acetabulum.

Once this reference point is known, the navigation system can constantly monitor the relative disposition of the tool to the pelvic bone and in particular to the reference point, and thus provide the surgeon with a possibility of controlling the guidance of the tool and the anatomically correct disposition of the receiving cavity in the pelvic bone that can be achieved as a result of this. In particular, it is possible to reduce the risk of machining the receiving cavity too deeply into the pelvic bone, so that too thin a bone wall remains in the region of the acetabulum or even an undesirable fenestration of the bone occurs.

It is advantageous if to determine the disposition of the plane of the pelvic inlet, the two anterior superior iliac spines of the pelvic bone as well as the pubic symphysis are approached by means of the navigated scanning instrument and the plane of the pelvic inlet is calculated from the position data of these three points.

Therefore, on this basis, anatomical features of the pelvic bone can also be utilised and this scanning of the three mentioned points can occur extracorporeally.

It is favourable if the height of the reference point above the tear-drop plane is selected as a function of the dimensioning of the tool and thus of the desired size of the receiving cavity in such a manner that the lower edge of the receiving cavity lies approximately in the tear-drop plane.

The receiving cavity is generally machined with a hemispherical cutter, so that the hemispherical receiving cavity is well defined in its height by this dimensioning.

In the case of a displacement in the cranial direction of the secondary acetabulum, in which the femur bone is seated in the pelvic bone prior to the operation, pre-operatively there results a shortening of the leg of the patient compared to the normal anatomical seating in the primary acetabulum, in which a femur would be seated in the case of an anatomically correct placement. If the new acetabulum is implanted in the region of the primary acetabulum, a lengthening of the leg necessarily results from this that is normally accepted. While it has been found that this lengthening of the leg up to a dimension of about 25 mm is unproblematic, problems can arise with a larger lengthening, in particular a lengthening of more than 40 mm, since the muscles and nerves are then stretched excessively. This can cause injuries and should be prevented.

Therefore, according to a preferred embodiment of the invention, it is provided that the height of the reference point above the tear-drop plane is selected such that a maximum value of the spacing between the height of the reference point and the position of a secondary acetabulum displaced in the cranial direction relative to the primary acetabulum is not exceeded. This maximum value should amount to 40 mm at maximum, preferably to 25 mm.

In this case it is advantageous if the maximum value is determined between a central point of the secondary acetabulum and the reference point.

According to a preferred embodiment, to determine the central point, the navigated femur bone can be moved pre-operatively in the secondary acetabulum relative to the navigated pelvic bone, the mid-point of the movement of the femur bone can be determined from the movement and this mid-point used as central point of the secondary acetabulum.

In an alternative procedure, to determine the central point, a navigated scanning instrument can be placed against the supporting surface of the secondary acetabulum and the position of the secondary acetabulum can be determined as a result of this, wherein from the disposition data of the secondary acetabulum the mid-point thereof is then determined as central point of the secondary acetabulum. Such a scanning instrument can either scan points of the supporting surface, or it is also possible to insert an approximately hemispherical abutment surface on the scanning instrument into the secondary acetabulum and thus determine the position data of the supporting surface of the secondary acetabulum.

It can be provided that the position of the reference point in the anterior-posterior direction is selected such that it lies approximately in the centre of the receiving cavity.

It is desirable to position the receiving cavity such that the dorsal edge region of the pelvic bone is fully retained at the height of the receiving cavity, i.e. is not removed by the tool generating the receiving cavity, since destruction or removal of this dorsal edge could adversely affect the fixture of the acetabulum in the receiving cavity. This dorsal edge is a bone protrusion of the pelvic bone and has a crescent shape.

To achieve this aim, according to a preferred embodiment it can be provided that the position data of one or more points of the dorsal edge of the pelvic bone in the region of the primary acetabulum are determined by means of a navigated probe and the receiving cavity is positioned such that the spacing of the edge of the receiving cavity from the position of the measurement point or the measurement points of the dorsal edge does not fall below a defined minimum value. If only a point of the dorsal edge is scanned with the probe, the spacing between this point and the edge of the receiving cavity is determined. However, if, according to a preferred embodiment, a plurality of measurement points are determined, then it can be provided that from the position data of this plurality of measurement points of the dorsal edge of the pelvic bone the one selected is that arranged furthest in the ventral direction, and then it is advantageous if the defined minimum value is determined from the position data of this selected measurement point. In this way, it is assured that even with a relatively imprecise acquisition of the position data of the dorsal edge, a maximum spacing from the dorsal edge is maintained and this is not damaged during creation of the receiving cavity.

When determining the position of the receiving cavity and when guiding the tool with which this receiving cavity is generated, the minimum spacing between the outer surface of the tool or the central point of the tool, on the one hand, and the selected measurement point, on the other hand, can be determined. However, according to a preferred embodiment it can also be provided that a dorsal frontal plane extending through a selected measurement point of the dorsal edge is determined and the defined minimum value between the edge of the receiving cavity and this dorsal frontal plane is determined. This dorsal frontal plane extends substantially parallel to the plane of the pelvic inlet and through the selected measurement point. If the outer surface of the tool or its central point maintains a specific spacing in relation to this dorsal frontal plane, it is also assured that no damage of the dorsal edge of the pelvic bone can occur.

It is particularly advantageous if the spacing of the reference point from the outer surface of the pelvic bone is determined from the position data of a navigated scanning instrument, which is inserted through an artificial opening in the region of the primary acetabulum of the pelvic bone in the medial direction through the pelvic bone as far as the rear side of the pelvic bone. Thus, working from the primary acetabulum a drill hole or opening is machined through the pelvic bone, so that the scanning instrument can be advanced as far as the rear side of the pelvic bone and can thus determine the maximum depth available inside the bone to machine the receiving cavity in place.

It is particularly favourable in this case if, to determine the spacing of the reference point from the outer surface of the pelvic bone, the scanning instrument is placed against the rear side of the pelvic bone by means of an abutment surface protruding laterally from a shaft. This abutment surface can be formed, for example, by a laterally protruding hook of the shaft. Such a scanning instrument can be pushed through the opening in the pelvic bone and then pulled back until the abutment surface abuts against the rear side of the pelvic bone. As a result of this, the thickness of the pelvic bone can be determined in this region and this position is used to determine the reference point.

When machining the receiving cavity in place it can be provided according to a first preferred embodiment that the tool is guided such that the shortest spacing of its outer surface serving to machine bone from the reference point does not fall below a defined value. Thus, it is ensured, for example, that the spherical outer surface of the cutter only approaches the reference point so far until a defined value is fallen below.

In a further preferred embodiment it can be provided that the tool is guided such that the shortest spacing of its central point from the reference point does not fall below a defined value. This is particularly favourable when hemispherical cutters with different radii are used in succession. The operating surgeon can then ensure that the central points of these milling cutters do not come excessively close to the reference point.

Instead of selecting the spacing of the outer surface of the tool or its central point in relation to the reference point as critical magnitude, it would also be possible to select the spacing of the outer surface or the central point in relation to a sagittal plane extending through this reference point. In each case, it is ensured that the spacings from the reference point or this sagittal plane do not fall short of a defined value in order to limit the depth of the receiving opening to a permissible dimension.

The invention also relates to a surgical navigation system for a navigated tool for producing a cavity to receive an acetabulum in a navigated pelvic bone with a navigated scanning instrument and with a data processing unit for processing the position data of the navigated parts.

It is an object of the invention to configure such a surgical navigation system so that the operating surgeon is provided with maximum assistance when guiding the machining tool for the receiving cavity.

This object is achieved according to the invention with a surgical navigation system of the above-described type in that the data processing unit is programmed in such a way that from the position data of the tear-drop point on the pelvic bone determined by means of a navigated scanning instrument and from the position data of the plane of the pelvic inlet, it determines a tear-drop plane, which lies perpendicular to said plane of the pelvic inlet and extends parallel to a line connecting the two anterior superior iliac spines and through the scanned tear-drop point, that it determines a reference point at a defined height above the tear-drop plane and in a defined position in the anterior-posterior direction and at a defined spacing from the outer surface of the pelvic bone in the lateral-medial direction, and that it calculates the disposition of the tool relative to the pelvic bone and relative to the reference point.

It is advantageous in this case if the data processing unit is programmed in such a way that it calculates the plane of the pelvic inlet from the position data of the two anterior superior iliac spines and the pubic symphysis of the pelvic bone determined by means of the scanning instrument.

In a preferred embodiment it is provided that the data processing unit is programmed in such a way that it calculates the height of the reference point above the tear-drop plane as a function of the dimensioning of the tool and thus of the desired size of the receiving cavity such that the lower edge of the receiving cavity lies approximately in the tear-drop plane.

According to a preferred embodiment it is advantageous if the data processing unit is programmed in such a way that it selects the height of the reference point above the tear-drop plane in such a manner that a maximum value of the spacing between the height of the reference point and the position of a secondary acetabulum displaced in the cranial direction relative to the primary acetabulum is not exceeded. This maximum value can amount to 40 mm, preferably 25 mm.

In this case the data processing unit can be programmed in such a way that the maximum value between a central point of the secondary acetabulum and the reference point is determined.

In this case, it can be provided that the data processing unit is programmed in such a way that from the position data of a navigated femur bone moved pre-operatively in the secondary acetabulum relative to the navigated pelvic bone, it determines the mid-point of the movement of the femur bone and uses this mid-point as central point of the secondary acetabulum.

Alternatively, it can be provided that the data processing unit is programmed in such a way that it determines the disposition of the secondary acetabulum from the position data of a navigated scanning instrument, which is placed against the supporting surface of the secondary acetabulum, and that from the position data of the secondary acetabulum it determines the mid-point thereof as central point of the secondary acetabulum. According to a further preferred embodiment it is provided that the data processing unit is programmed in such a way that it selects the position of the reference point in the anterior-posterior direction such that it lies approximately in the centre of the receiving cavity.

It is additionally advantageous if the data processing unit is programmed in such a way that from position data, which have been determined by placing a navigated probe on one or more measurement points of the dorsal edge of the pelvic bone in the region of the primary acetabulum, it determines a position of the receiving cavity such a way that the spacing of the edge of the receiving cavity from the position data of the measurement point or the measurement points of the dorsal edge does not fall below a defined minimum value.

The data processing unit can preferably be programmed in such a way that from the position data of a plurality of measurement points of the dorsal edge of the pelvic bone it selects the one arranged furthest in the ventral direction, and that it determines the defined minimum value from the position data of this selected measurement point.

In addition, the data processing unit can be programmed in such a way that it determines a dorsal frontal plane extending through a measurement point of the dorsal edge and determines the defined minimum value between the edge of the receiving cavity or the central point of the receiving cavity and this dorsal frontal plane.

It can be additionally provided that the data processing unit is programmed in such a way that it determines the spacing of the reference point from the outer surface of the pelvic bone from the position data of a navigated scanning instrument, which is inserted through an artificial opening in the region of the primary acetabulum of the pelvic bone in the medial direction through the pelvic bone as far as the rear side of the pelvic bone.

In this case, it is favourable if to determine the spacing of the reference point from the outer surface of the pelvic bone, the scanning instrument has an abutment surface protruding laterally from a shaft for placement against the rear side of the pelvic bone.

In a first preferred embodiment, it can be provided that the data processing unit is programmed in such a way that it calculates the shortest spacing of the outer surface of the tool serving to machine bone from the reference point.

Instead of the shortest spacing between the outer surface of the tool and the reference point, the shortest spacing between the central point of the tool and the reference point can be determined.

In other cases, these spacings are not determined in relation to the reference point, but in relation to a sagittal plane extending through the reference point.

It is additionally advantageous if the data processing unit is programmed in such a way that it displays the relative position of the tool and the reference point or the sagittal plane passing through the reference point on a display.

In addition, it is helpful for the operating surgeon if the data processing unit is programmed in such a way that it generates a warning signal as soon as the defined value is exceeded or fallen below. This ensures that the tool is not worked too deeply into the bone.

The above-described measures can be used in combination with one another in a particularly advantageous manner. However, it is also possible to use only some of these steps during preparation of the corresponding operation. This relates in particular to the determination of the disposition of the receiving cavity with respect to the height above the tear-drop plane, with respect to the spacing of the receiving cavity relative to the secondary acetabulum in the cranial direction, with respect to the spacing of the receiving cavity from the dorsal edge of the pelvic bone and with respect to the determination of the penetration depth of the receiving cavity by positioning a reference point in the pelvic bone or on the rear side of the pelvic bone. Each of these measures can be used advantageously individually, and several or all of these measures can also be applied jointly.

BRIEF DESCRIPTION OF THE DRAWINGS

The following description of preferred embodiments of the invention serves as a more detailed explanation in association with the drawing.

FIG. 1 is a view of an operating theatre with a navigation system and a patient as well as surgical instruments, which are provided with marking elements for the navigation system;

FIG. 2 is a schematic representation of a pelvic bone provided with a marking element and the scanning points used to determine the plane of the pelvic inlet;

DETAILED DESCRIPTION

Figure 3:
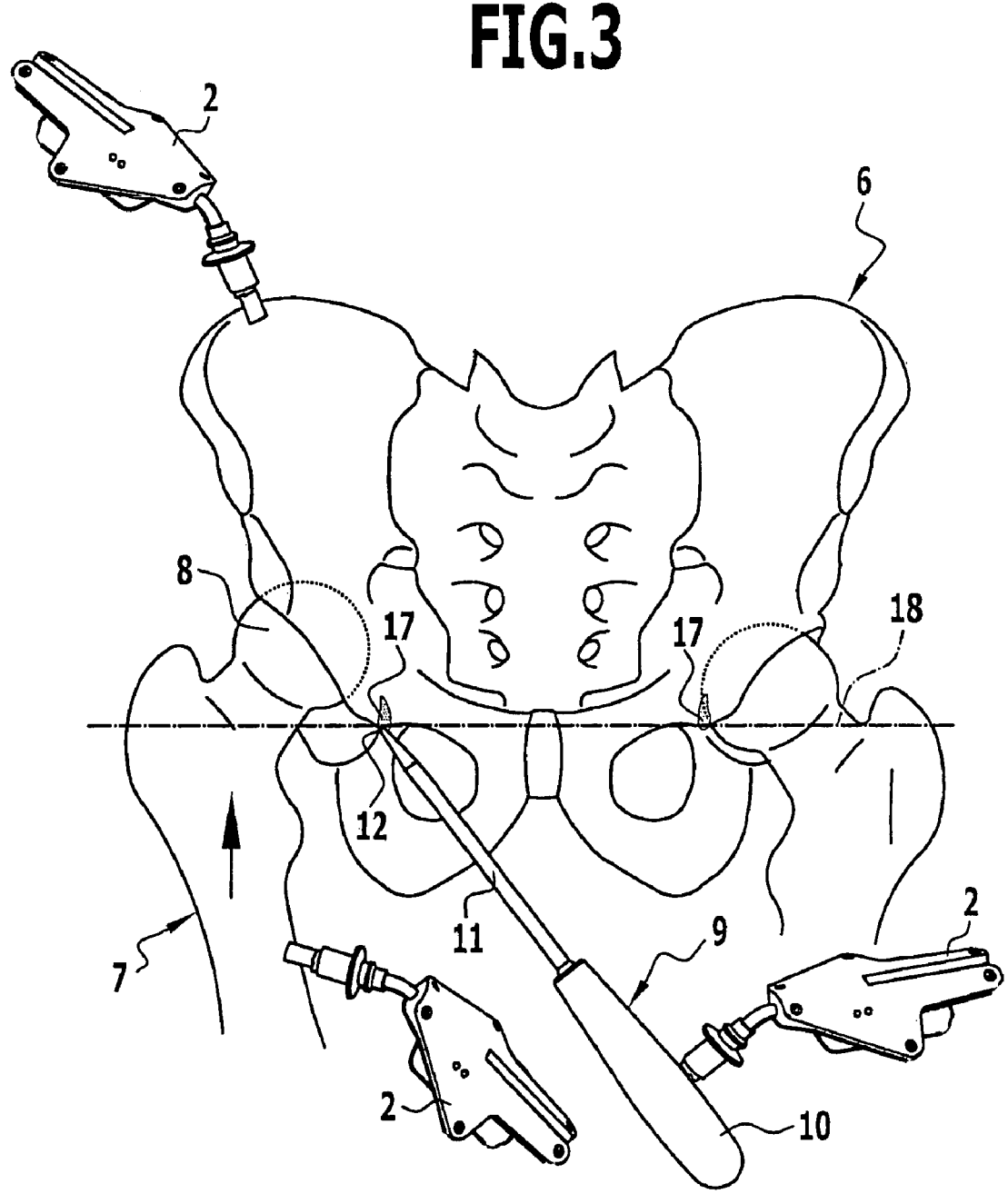
FIG. 3 is a schematic representation of the pelvic bone and a navigated scanning instrument during scanning of a tear-drop point.

To perform a hip joint implantation on a patient 1, a navigation system is used that can spatially determine the position and orientation—referred to jointly as disposition—of marking elements 2. These marking elements 2 can be fixedly connected to body parts, instruments etc., and therefore allow the disposition of these body parts and instruments to be spatially determined. In this case, the determination is achieved by means of stationary transmitters 3 that are spaced from one another and at the same time are configured as receivers and receive radiation emitted by them, which is reflected at spaced reflectors of the marking elements 2.

The position data of the marking elements 2 and thus of the body parts and instruments rigidly connected thereto are recorded in a data processing unit 4 and further processed, and these body parts and instruments can be represented in their disposition relative to one another on a screen 5 controlled by the data processing unit 4.

Figure 4:
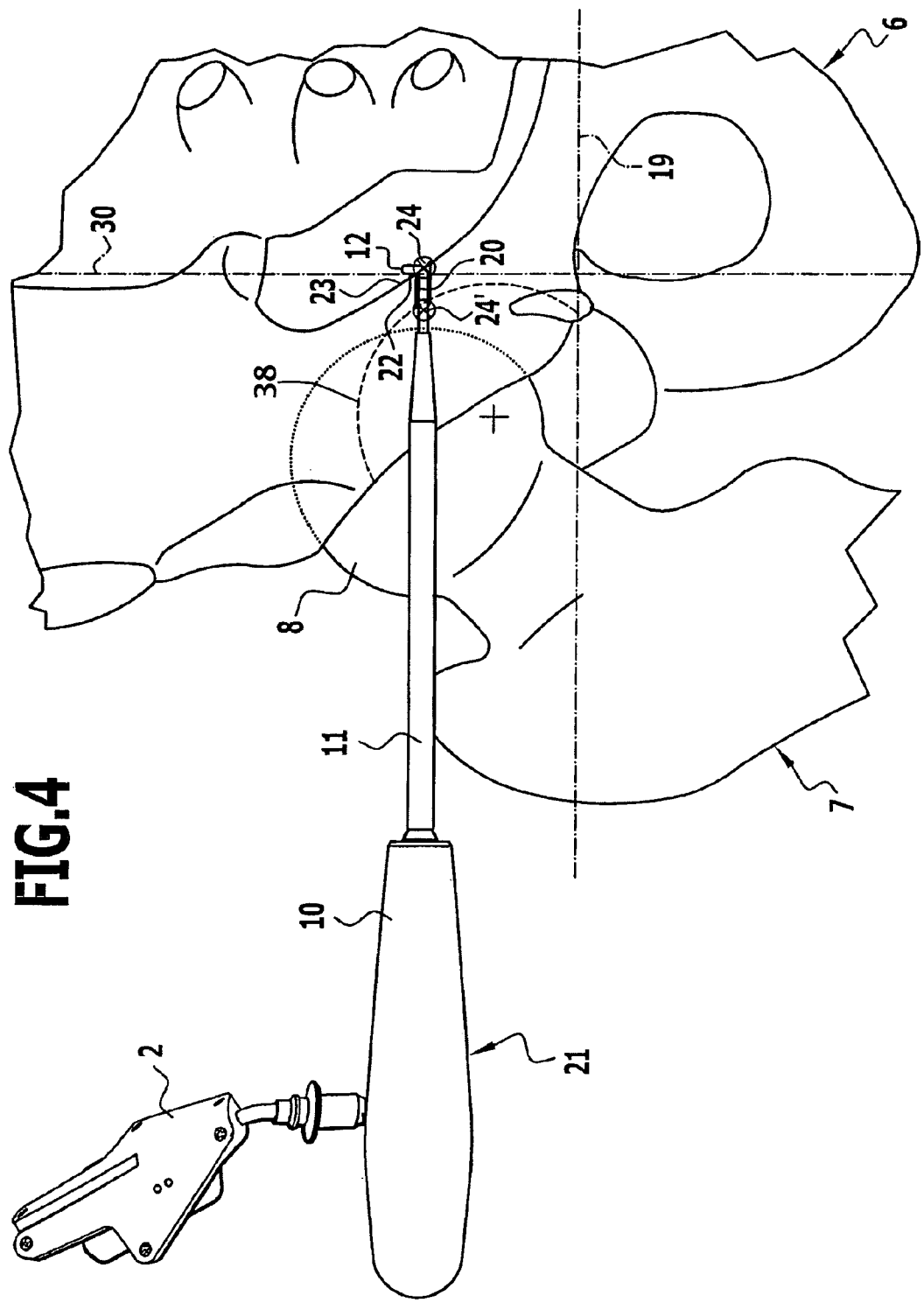
FIG. 4 is a schematic side view of the pelvic bone with a navigated scanning instrument inserted through an artificial opening in the region of the acetabulum.

FIG. 4 schematically shows a pelvic bone 6 together with the upper portion of a femur bone 7, which penetrates with a femoral head 8 into a natural acetabulum (not shown further in the drawing). In the example shown in FIG. 4, this acetabulum is displaced upwards relative to the normal anatomical position—i.e. in the cranial direction—the contour of this upwardly displaced acetabulum being identified by a row of dots.

During replacement of the hip joint the hip joint should be displaced downwards—i.e. in the caudal direction—so that it assumes the anatomically correct disposition in the pelvic bone. This anatomically correct disposition is indicated in FIG. 4 by a curved broken line. There thus results the task of finding and determining this anatomically correct disposition on the pelvic bone. The natural acetabulum cannot be referred to for this, since it is undefinably removed from the anatomical ideal position because of the pathological change.

It is therefore necessary to construct a reference system by means of specific prominent points on the pelvic bone, on the basis of which the disposition of the receiving cavity receiving the artificial acetabulum can be defined.

For this purpose, the pelvic bone 6 is rigidly connected once to a marking element 2, e.g. this can be screwed into the pelvic bone by means of a bone screw.

In addition, a scanning instrument 9 is used that also carries a marking element 2 and essentially has a handle 10 and an elongated shaft 11 with a tip 12 held thereon (FIG. 3).

The operating surgeon places the scanning instrument 9 against different prominent points of the pelvic bone 6 so that the tip 12 sits directly on these prominent points. This is possible through the skin that lies directly on the pelvic bone in these locations. This concerns the two anterior superior iliac spines 13, 14 on the upper side of the pelvic bone 6 and the pubic symphysis 15 on the underside of the pelvic bone 6 and in its centre. The position data of these three prominent points are fed by means of the navigated scanning instrument 9 to the data processing unit 4, which calculates a plane from these three points, namely the so-called plane of the pelvic inlet 16 (FIG. 2).

In a subsequent step a small protrusion in the vicinity of the hip joint, namely the so-called tear-drop point 17, is scanned with the aid of the scanning instrument 9 on the side of the pelvic bone, at which the implant is to be inserted. This point can be scanned relatively accurately and is so small that the position data of this point can be determined with high precision and fed to the data processing unit.

The data processing unit calculates a line that runs parallel to the connecting line of the two anterior superior iliac spines and passes through the scanned tear-drop point 17. The thus generated line is called the tear-drop line 18 and connects the two tear-drop points 17 on opposite sides of the pelvic bone 6.

From the position data of the plane of the pelvic inlet 16 and the position data of the tear-drop line 18, the data processing unit 4 now calculates a tear-drop plane 19, which lies perpendicular to the plane of the pelvic inlet 16 and in which the tear-drop line 18 lies. While the plane of the pelvic inlet 16 is a substantially perpendicular frontal plane when the pelvic bone 6 is upright, the tear-drop plane 19 runs substantially horizontally and passes through the two tear-drop points 17.

In a subsequent step, a drill hole is made in the pelvic bone 6 in the medial direction, through which the pelvic bone 6 is drilled from the outside inwards. This drill hole 20 runs substantially parallel to the tear-drop line 18 and at a height above the tear-drop plane 19 that lies approximately in the centre of the provided receiving cavity 38. This height can be estimated by way of the tools used, these tools being generally configured as hemispherical cutter heads, so that the size of the receiving cavity is also defined by the selection of a specific cutter head.

Thus, it is possible for the operating surgeon to estimate the height of the drill hole 20 above the tear-drop plane 19 within certain limits.

Figure 8:
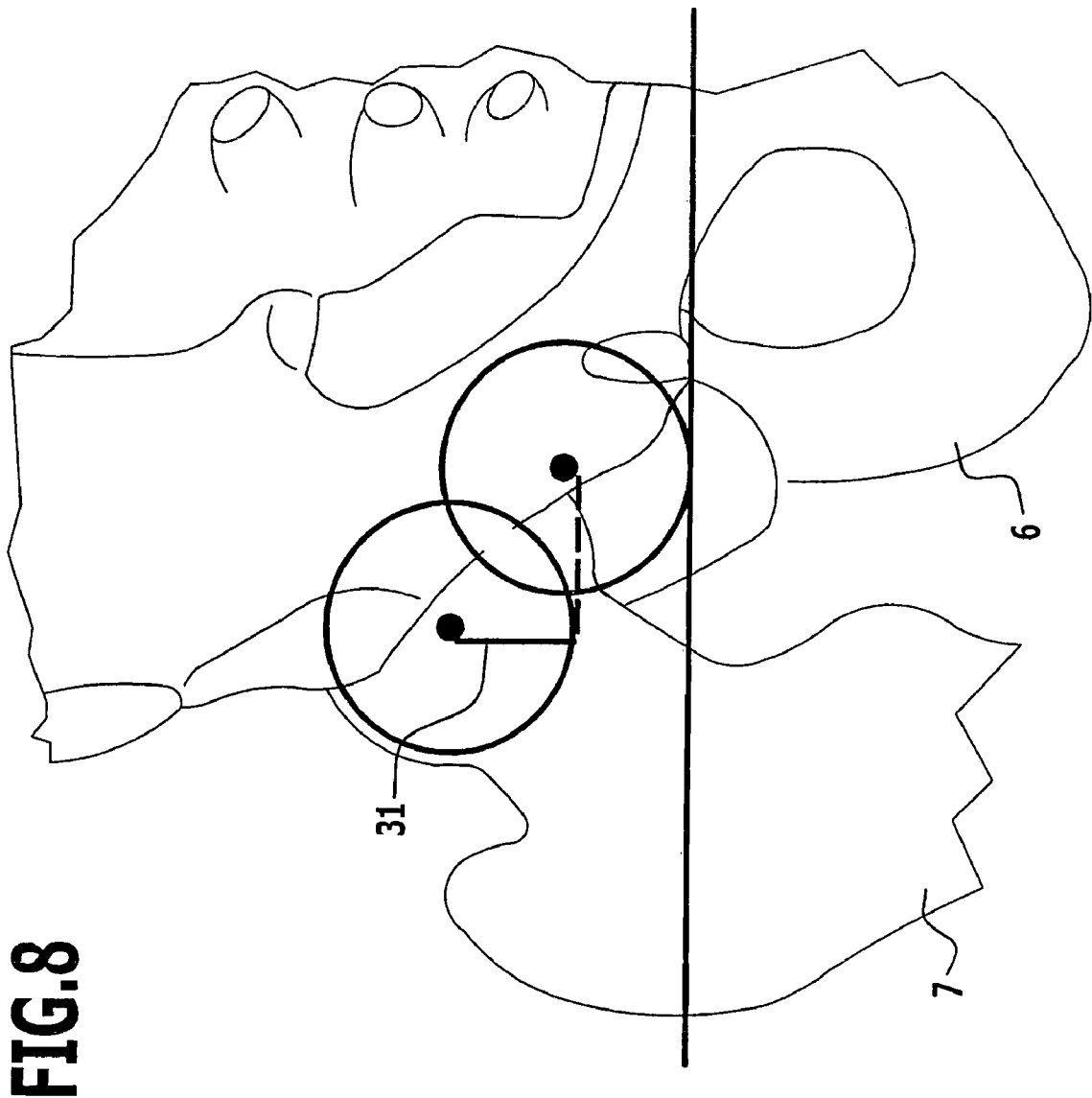
FIG. 8 is a schematic partial view of the pelvic bone with a primary and a secondary acetabulum and an indication of its spacing in the cranial direction.

When estimating the height of the drill hole 20 above the tear-drop plane 19, the position of the secondary acetabulum, in which the femur bone 7 is seated prior to the operation, should possibly also be taken into consideration. If the spacing of the primary acetabulum, in which the femur bone is to be seated after the operation, and the secondary acetabulum in the cranial direction exceeds a defined value, this can cause a displacement of the femur bone relative to the pelvic bone, in which case damages to the muscle tissue and the nerves could occur as a result of excessive extension. In order to prevent this, it is provided according to a preferred embodiment of the invention that the position of the secondary acetabulum on the pelvic bone and in particular the spacing from the tear-drop plane are determined. This can be achieved by means of the probe 9, with which points of the supporting surface of the secondary acetabulum are scanned. From these position data and the assumption that this supporting surface is approximately spherical in configuration, the data processing unit can calculate the central point of the secondary acetabulum and from this a spacing of the central points of the primary acetabulum from the secondary acetabulum. This displacement is identified by the reference 31 in FIG. 8.

It can be provided that the value of this displacement must not exceed a maximum value, i.e. a value between 25 and 40 mm, for example, preset by the operating surgeon him/herself. As a result of this, a correction of the disposition of the primary acetabulum can occur such that the height of the primary acetabulum above the tear-drop plane becomes greater, i.e. the edge of the primary acetabulum no longer falls within the tear-drop plane, but lies above this.

Figure 7:
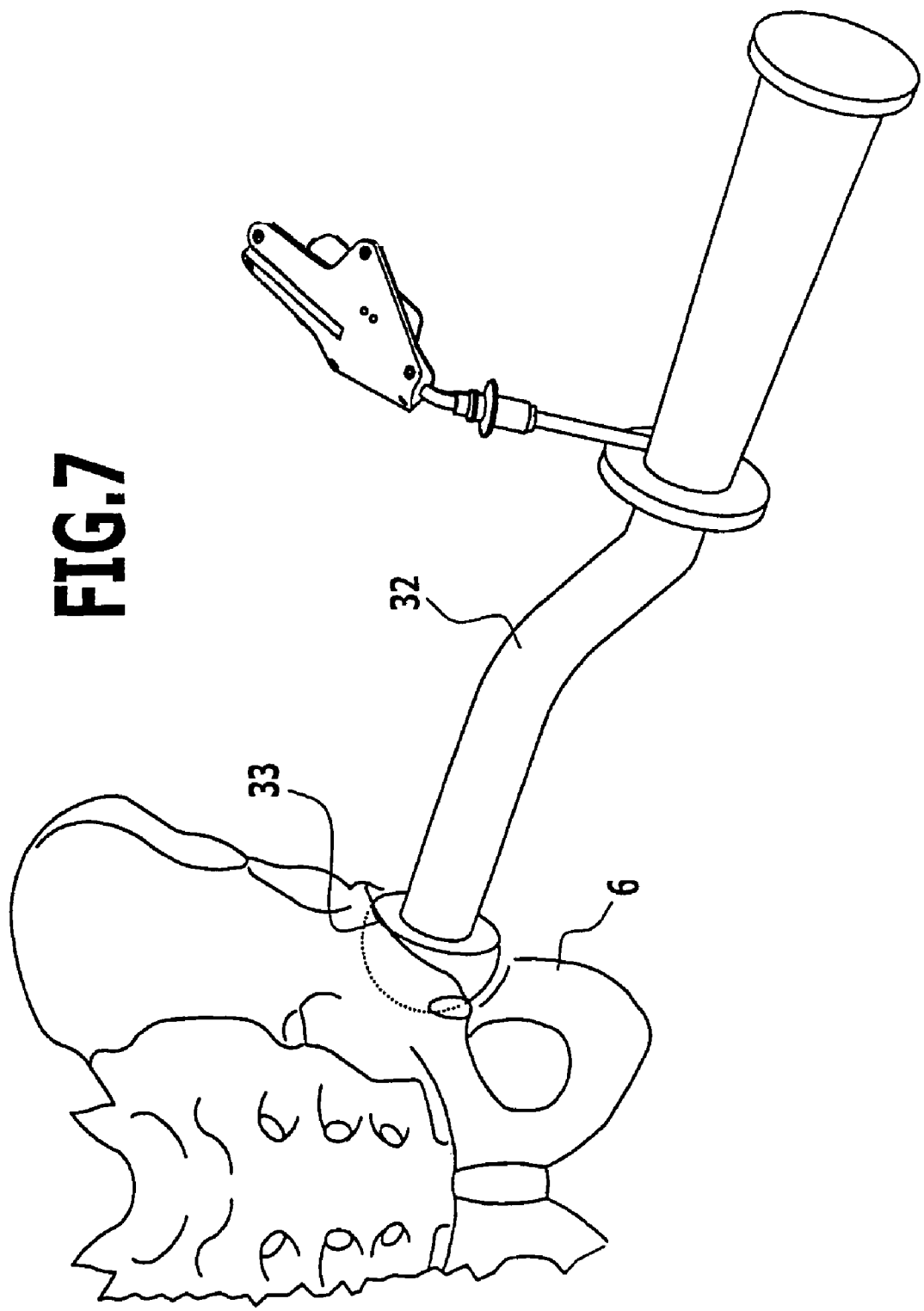
FIG. 7 is a schematic view of a pelvic bone with a scanning instrument inserted into the secondary acetabulum to determine the position data of the secondary acetabulum.

The disposition of the secondary acetabulum could also be determined with a navigated test implant or a navigated probe with a spherical abutment surface, as is shown in FIG. 7. Such a probe 32 is inserted into the secondary acetabulum at the spherical abutment surface 33. The data processing unit can then determine the central point of the spherical abutment surface 33 from the course thereof and use the position data of this central point as the centre of the secondary acetabulum for determination of the spacing from the primary acetabulum. The drill hole 20 is arranged in the anterior-posterior direction such that it also runs substantially in the centre of the receiving cavity to be created. This can also be estimated, so that the operating surgeon can determine the entry point and the direction of the drill hole 20. This is preferably assisted by the scanning instrument 9, namely the operating surgeon can bring the scanning instrument, which is navigated, into the corresponding disposition and then mark an entry point for the drill hole 20, e.g. by light hammer taps.

Figure 6:
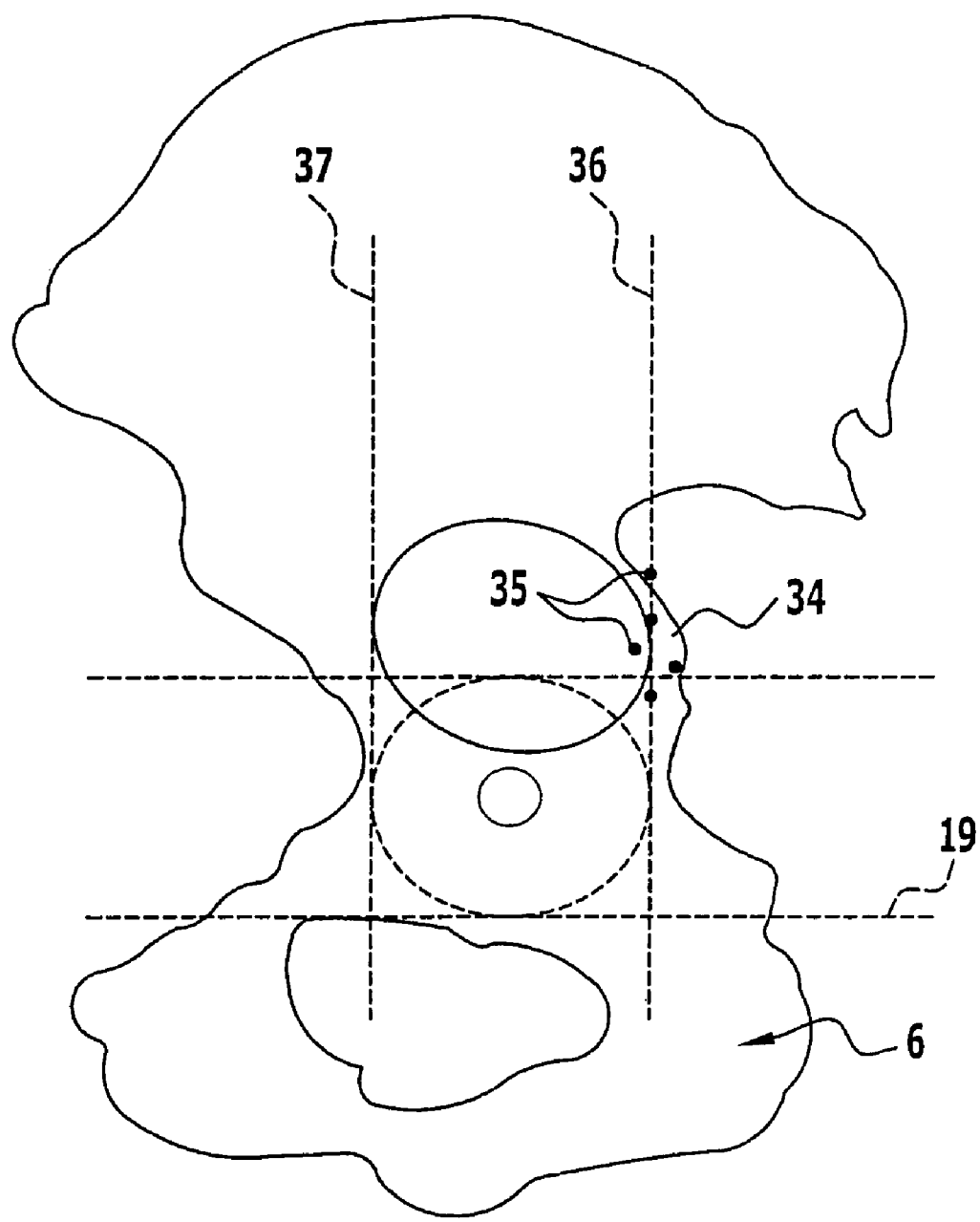
FIG. 6 is a lateral view of a pelvic bone with measurement points on the dorsal edge of the pelvic bone and with indications of the disposition of the tear-drop plane, a ventral and a dorsal frontal plane as well as the disposition of a primary and a secondary acetabulum.

The receiving cavity should be positioned in such a manner that the crescent-shaped dorsal edge 34 configured as a bone protrusion (FIG. 6) is not damaged when the receiving cavity is created. To achieve this, it can be provided that the operating surgeon scans one or more measurement points 35 on the dorsal edge 34 with the scanning instrument 9 and thus transfers the position data thereof to the data processing unit. This scanning is not very precise in some circumstances, since the dorsal edge 34 has a certain expanse and since it can be difficult to reach the dorsal edge over its entire expanse in the surgical wound.

Therefore, the data processing unit can be programmed in such a manner that when scanning a specific number of measurement points 35, it selects the measurement point that is shifted the most in the ventral direction.

If only one measurement point has been determined, or if the most ventral measurement point has been selected from a plurality of measurement points in the described manner, the data processing unit can then place a dorsal frontal plane 36 running parallel to the plane of the pelvic inlet through this measurement point and use this dorsal frontal plane 36 to determine the position of the receiving cavity in the anterior-posterior direction. Namely, the receiving cavity is positioned in such a manner that the edge of the receiving cavity or the central point of this dorsal frontal plane 36 must not fall below a minimum value, and in any case this is selected so that the receiving cavity does not damage the dorsal edge 34.

It would be possible in principle to also determine measurement points on the ventral edge of the pelvic bone 4 in the same way and to determine a ventral frontal plane 37 there, so that the area, in which the receiving cavity must extend, is confined. This can also cause the size of the tools used for creating the receiving cavity and therefore the size of the implanted sockets to be restricted.

Therefore, as a result of the tear-drop plane and possibly the dorsal frontal plane as well as possibly a ventral frontal plane, geometric data are made available to the operating surgeon, with which he/she can precisely pre-plan the positioning of the receiving cavity and can then also achieve this, and this arrangement can be corrected by the boundary condition, according to which the spacing between the secondary acetabulum and the primary acetabulum should not exceed a defined value.

If the data are determined in the described manner, the drill hole 20 is made carefully in the pelvic bone with a drill that is not shown in the drawing in order to prevent a sudden breakthrough and therefore any injury to the soft tissue inside the pelvic bone.

The drill hole 20 is used to determine the thickness of the pelvic bone 6 in the area of the drill hole 20. For this, a further scanning instrument 21 that also carries a marking element 2 and can thus be navigated is inserted through the drill hole 20. This is configured in a similar manner to the scanning instrument 9, and therefore the same parts are given the same reference numerals. Only the tip 12 is bent at right angles, so that on the inside of the bent tip 12 an abutment surface 22 is configured, which can be placed against the rear side 23 of the pelvic bone 6 when the scanning instrument 21 is inserted through the drill hole 20 and when subsequently removing it (FIG. 4). The position of this rear side 23 that at the same time is a dimension for the thickness of the pelvic bone 6 can be determined as a result of this.

The exit point of the drill hole 20 on the rear side 23 obtained in this way is selected as reference point 24 for the following procedure.

In a slightly modified method not explained in more detail, such a reference point 24' is obtained in a slightly modified manner by approaching the point, which is defined above as the entry point of the drill hole 20, with a navigated scanning instrument. Such a point inside the pelvic bone 6 can be determined, for example, by advancing the scanning instrument 9 in the medial direction in the area of the receiving cavity to be created in the same position as the drill hole 20, but not quite so far that the scanning instrument penetrates the pelvic bone.

Therefore, in this case the reference point 24' will lie inside the pelvic bone 6.

Figure 5:
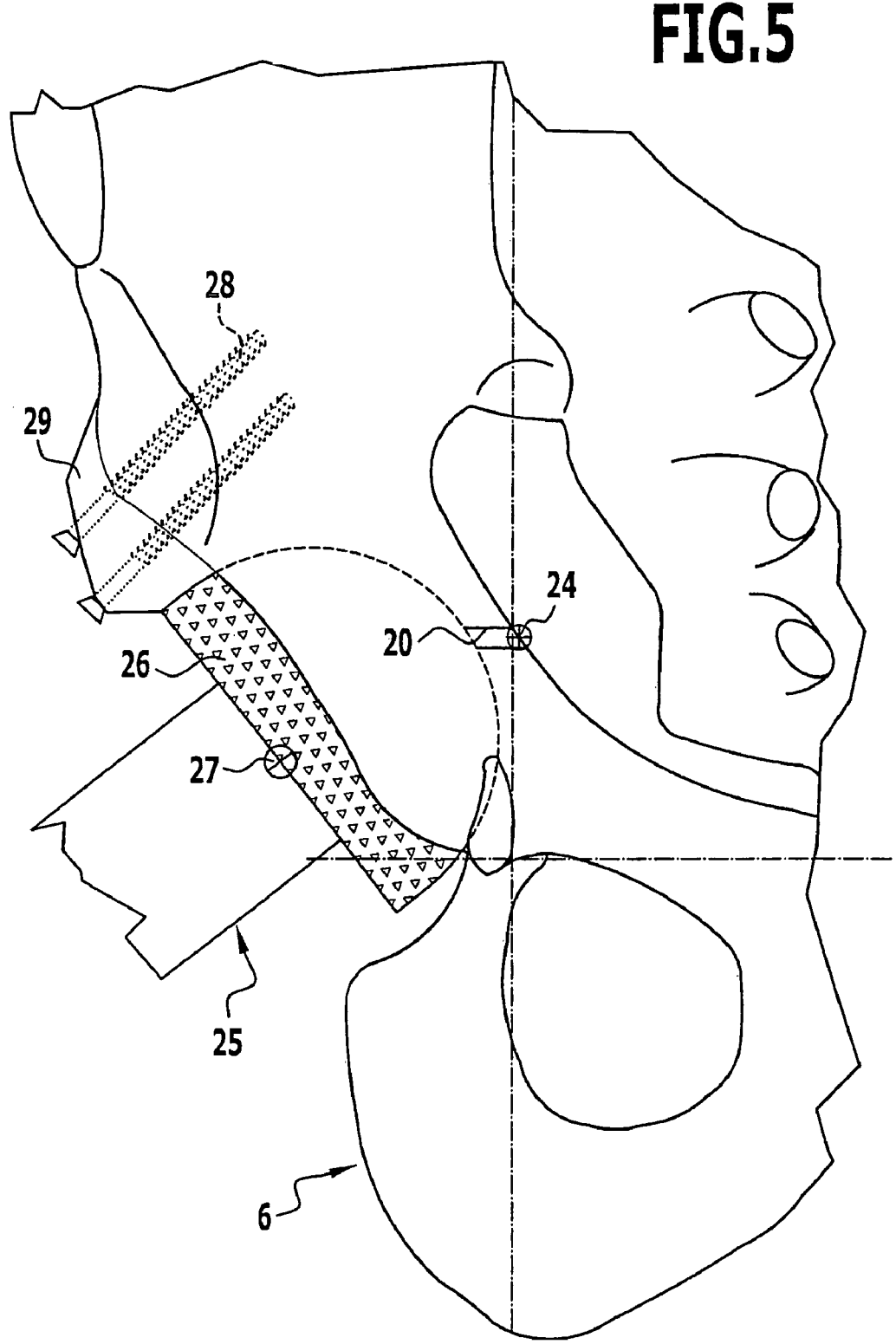
FIG. 5 is a side view of a pelvic bone during machining of a receiving cavity by means of a hemispherical cutter.

In both cases, this reference point 24 or 24' serves to provide the operating surgeon with a measure, as to how he/she must advance a tool 25, i.e. the hemispherical cutter head shown in FIG. 5, for example, in order to generate a receiving cavity in the desired position and with the desired depth in the pelvic bone 6.

From the marking element, which is screwed into the pelvic bone 6, the data processing unit receives information relating to the disposition of the pelvic bone and from this can calculate the disposition of the reference point 24 or 24', the navigated tool 25 likewise transfers its position data to the data processing unit by means of the marking element connected to it, and thus it can be displayed on the screen 15 how the tool 25 is being advanced relative to the pelvic bone 6. The tear-drop plane 19 and/or the tear-drop line 18 can also be copied into the display, if need be.

Other data can, of course, also be displayed on the screen, e.g. the disposition of the primary and the secondary acetabulum, the position of the measurement points 35, the disposition of the dorsal frontal plane 36 or possibly of a ventral frontal plane 37, and also the data of the spacing 31 between the primary and the secondary acetabulum in the cranial direction.

As the tool 25 advances, the operating surgeon sees how this is oriented relative to the said planes and thus to the pelvic bone and how deeply the tool is penetrating the pelvic bone.

The data processing unit can additionally determine the spacing of the outer surface 26 of the tool 25 or the central point 27 of the tool 25 from the reference points 24 or 24', and thus obtains a measure for the penetration depth of the tool 25. Instead of a direct determination of the spacing in relation to the reference points 24, 24', the data processing unit can also determine a sagittal plane, which extends through reference point 24 or reference point 24'. This is essentially a plane that lies perpendicular both to the plane of the pelvic inlet and the tear-drop plane.

In each case, the data processing unit will monitor adherence to the limit values between the tool (outer surface or central point) and the geometric planes or points, which have been determined in the above-mentioned manner. As soon as a deviation from the extreme values occurs, the data processing unit will emit a warning and thus prevent the operating surgeon from directing the tool in an undesirable manner, i.e. for example, driving it too deeply into the pelvic bone, working too closely to the dorsal edge 34 or aiming at too large a spacing from the secondary acetabulum.

When displacing the bone cavity in the caudal direction, it is necessary in some circumstances to fill part of the natural cavity of the secondary acetabulum with a bone implant in order to provide the possibility of being able to generate a receiving cavity arranged completely in the bone material in a position located at a deeper level. This is usually achieved by inserting bone implants in the area of the original natural receiving cavity; this is indicated in FIG. 5 by a bone implant 29 held on the pelvic bone 6 by means of bone screws 28. This can be formed, for example, from the correspondingly machined and resected femoral head.

What is claimed is:

1. A method for creating a receiving cavity to receive an acetabulum in a navigated pelvic bone with the aid of a navigated tool, comprising:
    determining position data of two anterior superior iliac spines of the pelvic bone and of a pubic symphysis by means of a navigated scanning instrument,
    determining a plane of a pelvic inlet from the position data of the two anterior superior iliac spines of the pelvic bone and the pubic symphysis,
    locating a tear-drop point on the pelvic bone by means of the navigated scanning instrument,
    determining position data of the located tear-drop point;
    determining a tear-drop plane from the position data of the tear-drop point and the plane of the pelvic inlet of said pelvic bone, which tear-drop plane lies perpendicular to said plane of the pelvic inlet and extends parallel to a line connecting the two anterior superior iliac spines and running through the located tear-drop point,
    determining a position of a secondary acetabulum by means of the navigated scanning instrument, the secondary acetabulum comprising an actual position of an acetabulum of a patient which is displaced in a cranial direction relative to a primary acetabulum comprising a correct positioning of the acetabulum,
    determining a reference point at a defined height above the tear-drop plane and in a defined position in an anterior-posterior direction and at a defined spacing from an outer surface of the pelvic bone in a lateral-medial direction,
    the height of the reference point above the tear-drop plane being selected such that a maximum value of a spacing between the height of the reference point and the position of the secondary acetabulum is not exceeded, and
    working the tool into the pelvic bone in a desired direction relative to the reference point until a predetermined disposition of the tool relative to the reference point is reached.

2. A method according to claim 1, wherein the height of the reference point above the tear-drop plane is further selected as a function of a dimensioning of the tool and a desired size of the receiving cavity to be created by the tool in such a manner that a lower edge of the receiving cavity lies approximately in the tear-drop plane.

3. A method according to claim 1, wherein the maximum value amounts to 40 mm.

4. A method according to claim 1, wherein the maximum value amounts to 25 mm.

5. A method according to claim 1, wherein the maximum value is determined between a central point of the secondary acetabulum and the reference point.

6. A method according to claim 5, wherein to determine the central point:
    a navigated femur bone is moved pre-operatively in the secondary acetabulum relative to the navigated pelvic bone,
    a mid-point of the movement of the femur bone is determined, and
    the mid-point is used as the central point of the secondary acetabulum.

7. A method according to claim 5, wherein:
    to determine the central point, a navigated scanning instrument is placed against a supporting surface of the secondary acetabulum and a disposition of the secondary acetabulum is determined, and
    from position data of the secondary acetabulum a mid-point of the secondary acetabulum is determined as the central point of the secondary acetabulum.

8. A method according to claim 1, wherein the position of the reference point in the anterior-posterior direction is selected such that the reference point lies approximately in a center of the receiving cavity.

9. A method according to claim 1, wherein:
    position data of one or more measurement points of a dorsal edge of the pelvic bone in a region of the primary acetabulum are determined by means of a navigated probe, and
    the receiving cavity is positioned such that a spacing of an edge of the receiving cavity from the position data of the one or more measurement points of the dorsal edge does not fall below a defined minimum value.

10. A method according to claim 9, wherein:
    from the position data of a plurality of measurement points of the dorsal edge of the pelvic bone a measurement point selected is that the measurement point arranged furthest in a ventral direction, and
    the defined minimum value is determined from the position data of the selected measurement point.

11. A method according to claim 9, wherein:
    a dorsal frontal plane extending through one of the measurement points of the dorsal edge is determined, and
    the defined minimum value between the edge of the receiving cavity and the dorsal frontal plane is determined.

12. A method according to claim 1, wherein:
    the spacing of the reference point from the outer surface of the pelvic bone is determined from position data of a navigated scanning instrument, which is inserted through an artificial opening in a region of the primary acetabulum of the pelvic bone in a medial direction through the pelvic bone as far as a rear side of the pelvic bone.

13. A method according to claim 12, wherein to determine the spacing of the reference point from the outer surface of the pelvic bone the scanning instrument is placed against the rear side of the pelvic bone by means of an abutment surface protruding laterally from a shaft.

14. A method according to claim 1, wherein the tool is guided such that a shortest spacing of an outer surface of the tool serving to machine bone from the reference point does not fall below a defined value.

15. A method according to claim 1, wherein the tool is guided such that a shortest spacing of a central point of the tool from the reference point does not fall below a defined value.

16. A method according to claim 1, wherein the tool is guided such that a shortest spacing of an outer surface of the tool serving to machine bone from a sagittal plane extending through the reference point does not fall below a defined value.

17. A method according to claim 1, wherein the tool is guided such that a shortest spacing of a central point of the tool from a sagittal plane extending through the reference point does not fall below a defined value.

18. A surgical navigation system for a navigated tool for producing a receiving cavity to receive an acetabulum in a navigated pelvic bone, comprising:
   a navigated scanning instrument, and
   a data processing unit for processing position data of navigated bone structures,
   wherein the data processing unit is programmed to:
      determine position data of two anterior superior iliac spines of the pelvic bone and of a pubic symphysis,
      determine a plane of a pelvic inlet from the position data of the two anterior superior iliac spines of the pelvic bone and of the pubic symphysis,
      determine position data of a tear-drop point on the pelvic bone,
      determine determines a tear-drop plane from the position data of the tear-drop point and the plane of the pelvic inlet of said pelvic bone, which tear-drop plane lies perpendicular to said plane of the pelvic inlet and extends parallel to a line connecting the two anterior superior iliac spines and running through the tear-drop point,
      determine a position of a secondary acetabulum, the secondary acetabulum comprising an actual position of an acetabulum of a patient which is displaced in a cranial direction relative to a primary acetabulum comprising a correct positioning of the acetabulum,
      determine a reference point at a defined height above the tear-drop plane and in a defined disposition in an anterior-posterior direction and at a defined spacing from an outer surface of the pelvic bone in a lateral-medial direction, the height of the reference point above the tear-drop plane being selected such that a maximum value of a spacing between the height of the reference point and the position of the secondary acetabulum is not exceeded, and
      calculate a disposition of the tool relative to the pelvic bone and relative to the reference point.

19. A surgical navigation system according to claim 18, wherein the height of the reference point above the tear-drop plane is further calculated as a function of a dimensioning of the tool and a desired size of the receiving cavity to be created by the tool such that a lower edge of the receiving cavity lies approximately in the tear-drop plane.

20. A surgical navigation system according to claim 18, wherein the maximum value amounts to 40 mm.

21. A surgical navigation system according to claim 18, wherein the maximum value amounts to 25 mm.

22. A surgical navigation system according to claim 18, wherein the maximum value is determined between a central point of the secondary acetabulum and the reference point.

23. A surgical navigation system according to claim 22, wherein to determine the central point:
   a navigated femur bone is moved pre-operatively in the secondary acetabulum relative to the navigated pelvic bone, and
   the data processing unit determines a mid-point of the movement of the femur bone and uses this mid-point as the central point of the secondary acetabulum.

24. A surgical navigation system according to claim 23, wherein the data processing unit displays a relative disposition of the tool and the secondary acetabulum on a display.

25. A surgical navigation system according to claim 22, wherein:
   the data processing unit determines a disposition of the secondary acetabulum from position data of a navigated scanning instrument, which is placed against a supporting surface of the secondary acetabulum, and
   from the position data of the secondary acetabulum the data processing unit determines the mid-point of the secondary acetabulum as the central point of the secondary acetabulum.

26. A surgical navigation system according to claim 18, wherein the data processing unit calculates the position of the reference point in the anterior-posterior direction such that the reference point lies approximately in a center of the receiving cavity.

27. A surgical navigation system according to claim 18, wherein from position data of one or more measurement points which have been determined by placing a navigated probe against one or more measurement points of a dorsal edge of the pelvic bone in the region of a primary acetabulum, the data processing unit determines a position of the receiving cavity such that a spacing of an edge of the receiving cavity from the one or more measurement points of the dorsal edge does not fall below a defined minimum value.

28. A surgical navigation system according to claim 27, wherein:
   from the position data of a plurality of measurement points of the dorsal edge of the pelvic bone the data processing unit selects a measurement point that is arranged furthest in a ventral direction, and
   the data processing unit determines the defined minimum value from the position data of the selected measurement point.

29. A surgical navigation system according to claim 27, wherein the data processing unit determines a dorsal frontal plane extending through one of the measurement points of the dorsal edge and determines the defined minimum value between the edge of the receiving cavity and the dorsal frontal plane.

30. A surgical navigation system according to claim 27, wherein the data processing unit displays a relative disposition of the tool and the one or more measurement points of the dorsal edge of the pelvic bone and/or a dorsal frontal plane on a display.

31. A surgical navigation system according to claim 18, wherein the data processing unit determines the spacing of the reference point from the outer surface of the pelvic bone from position data of a navigated scanning instrument, which is inserted through an artificial opening in a region of the primary acetabulum of the pelvic bone in a medial direction through the pelvic bone as far as a rear side of the pelvic bone.

32. A surgical navigation system according to claim 31, wherein to determine the spacing of the reference point from the outer surface of the pelvic bone the scanning instrument has an abutment surface protruding laterally from a shaft for placement against the rear side of the pelvic bone.

33. A surgical navigation system according to claim 32, wherein the data processing displays a relative disposition of the tool and the reference point or a sagittal plane defined by the reference point on a display.

34. A surgical navigation system according to claim 18, wherein the data processing unit calculates a shortest spacing of an outer surface of the tool serving to machine bone from the reference point.

35. A surgical navigation system according to claim 18, wherein the data processing unit calculates a shortest spacing of a central point of the tool from the reference point.

36. A surgical navigation system according to claim 18, wherein the data processing unit calculates a shortest spacing of an outer surface of the tool serving to machine bone from a sagittal plane extending through the reference point.

37. A surgical navigation system according to claim 18, wherein the data processing unit calculates a shortest spacing of a central point of the tool from a sagittal plane extending through the reference point.

38. A surgical navigation system according to claim 18, wherein the data processing generates a warning signal as soon as critical values are exceeded or fallen below.

* * * * *